United States Patent
Kozloski et al.

(10) Patent No.: US 10,130,303 B2
(45) Date of Patent: *Nov. 20, 2018

(54) AUTOMATIC ADJUSTMENT OF HELMET PARAMETERS BASED ON A CATEGORY OF PLAY

(71) Applicant: INTERNATIONAL BUSINESS MACHINES CORPORATION, Armonk, NY (US)

(72) Inventors: James R. Kozloski, New Fairfield, CT (US); Mark C. H. Lamorey, Williston, VT (US); Clifford A. Pickover, Yorktown Heights, NY (US); John J. Rice, Mohegan Lake, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 713 days.

This patent is subject to a terminal disclaimer.

(21) Appl. No.: 14/709,574

(22) Filed: May 12, 2015

(65) Prior Publication Data

US 2016/0331318 A1 Nov. 17, 2016

(51) Int. Cl.
*A61B 5/00* (2006.01)
*A61F 5/37* (2006.01)
(Continued)

(52) U.S. Cl.
CPC ............ *A61B 5/6803* (2013.01); *A42B 3/046* (2013.01); *A42B 3/0433* (2013.01); *A42B 3/324* (2013.01);
(Continued)

(58) Field of Classification Search
CPC ....... A42B 3/0433; A42B 3/046; A42B 3/324; A61B 2503/10; A61B 2503/22;
(Continued)

(56) References Cited

U.S. PATENT DOCUMENTS 5,708,988 A * 1/1998 McGuine ............... A42B 3/145
2/417
6,007,086 A 12/1999 Hopkins
(Continued)

FOREIGN PATENT DOCUMENTS

CA 2772644 A1 6/2012

OTHER PUBLICATIONS

Funk et al., "Validation of Concussion Risk Curves for Collegiate Football Players Derived from HITS Data", Annals of Biomedical Engineering, vol. 40, No. 1, Jan. 2012; pp. 79-89.
(Continued)

*Primary Examiner* — Nader Bolourchi
(74) *Attorney, Agent, or Firm* — Cantor Colburn LLP; Vazken Alexanian

(57) ABSTRACT

Embodiments include method, systems and computer program products for automatic adjustment of helmet parameters based on a category of play. Aspects include monitoring a plurality of sensors in a helmet and determining the category of play for a user of the helmet based on data received from the plurality of sensors. Aspects further include automatically adjusting one or more parameters of the helmet based on the category of play.

11 Claims, 5 Drawing Sheets

(51) Int. Cl.
*A42B 3/04* (2006.01)
*A42B 3/32* (2006.01)
*A61B 5/11* (2006.01)

(52) U.S. Cl.
CPC .......... *A61B 5/1123* (2013.01); *A61F 5/3707* (2013.01); *A61B 5/4064* (2013.01); *A61B 5/7275* (2013.01); *A61B 2503/10* (2013.01); *A61B 2503/22* (2013.01)

(58) Field of Classification Search
CPC ... A61B 5/1123; A61B 5/4064; A61B 5/6803; A61B 5/7275; A61F 5/3707
See application file for complete search history.

(56) References Cited

U.S. PATENT DOCUMENTS

| | | | |
|---|---|---|---|
| 7,526,389 B2 | 4/2009 | Greenwald et al. | |
| 8,621,673 B1 | 1/2014 | Pietrantonio | |
| 2002/0183657 A1* | 12/2002 | Socci | A61B 5/1114 600/595 |
| 2005/0067816 A1* | 3/2005 | Buckman | A41D 13/018 280/730.1 |
| 2005/0177929 A1* | 8/2005 | Greenwald | A42B 3/046 2/425 |
| 2008/0158502 A1* | 7/2008 | Becker | A61F 9/067 351/44 |
| 2010/0101005 A1 | 4/2010 | Cripton et al. | |
| 2010/0140241 A1* | 6/2010 | Martin | A61F 9/065 219/130.21 |
| 2011/0144539 A1 | 6/2011 | Ouchi | |
| 2011/0215931 A1* | 9/2011 | Callsen | F41H 1/04 340/573.1 |
| 2012/0210498 A1 | 8/2012 | Mack | |
| 2012/0297525 A1 | 11/2012 | Bain | |
| 2013/0060489 A1 | 3/2013 | Crossman et al. | |
| 2013/0074248 A1* | 3/2013 | Evans | G08B 21/02 2/421 |
| 2013/0185837 A1 | 7/2013 | Phipps et al. | |
| 2014/0130239 A1 | 5/2014 | Preston-Powers | |
| 2014/0173812 A1 | 6/2014 | Krueger | |
| 2016/0125653 A1* | 5/2016 | Denis | B23K 9/322 348/90 |
| 2016/0278633 A1 | 9/2016 | Kozloski et al. | |
| 2016/0278666 A1 | 9/2016 | Kozloski et al. | |
| 2016/0278684 A1 | 9/2016 | Kozloski et al. | |
| 2016/0278685 A1 | 9/2016 | Kozloski et al. | |
| 2016/0278686 A1 | 9/2016 | Kozloski et al. | |
| 2016/0278693 A1 | 9/2016 | Kozloski et al. | |
| 2016/0331060 A1 | 11/2016 | Kozloski et al. | |
| 2016/0331295 A1 | 11/2016 | Kozloski et al. | |
| 2016/0331296 A1 | 11/2016 | Kozloski et al. | |
| 2016/0331302 A1 | 11/2016 | Kozloski et al. | |
| 2016/0331317 A1 | 11/2016 | Kozloski et al. | |
| 2016/0331319 A1 | 11/2016 | Kozloski et al. | |
| 2016/0331327 A1 | 11/2016 | Kozloski et al. | |
| 2016/0331355 A1 | 11/2016 | Kozloski et al. | |
| 2016/0331581 A1 | 11/2016 | Kozloski et al. | |
| 2016/0331582 A1 | 11/2016 | Kozloski et al. | |
| 2016/0335396 A1 | 11/2016 | Kozloski et al. | |
| 2016/0335398 A1 | 11/2016 | Kozloski et al. | |
| 2016/0335872 A1 | 11/2016 | Kozloski et al. | |

OTHER PUBLICATIONS

Rowson et al., "Development of the STAR Evaluation System for Football Helmets: Integrating Player Head Impact Exposure and Risk of Concussion", Annals of Biomedical Engineering, vol. 39, No. 8, Aug. 2011; pp. 2130-2140.

List of IBM Patents or Patent Applications Treated As Related—Date Filed: Feb. 21, 2018; 2 pages.

\* cited by examiner

AUTOMATIC ADJUSTMENT OF HELMET PARAMETERS BASED ON A CATEGORY OF PLAY

RELATED APPLICATIONS

This application is related to: U.S. Application No. 14/709,575; Filed: May 12, 2015; U.S. Application Ser. No.: 14/709,572; Filed: May 12, 2015; U.S. Application Serial No.: 14/709,570; Filed: May 12, 2015; U.S. Application Ser. No.: 14/709,563; Filed: May 12, 2015; U.S. Application Ser. No.: 14/709,568; Filed: May 12, 2015; U.S. Application Ser. No.: 14/709,564; Filed: May 12, 2015; U.S. Application Ser. No.: 14/664,987; Filed Mar. 23, 2015; U.S. Application Ser. No.: 14/664,989; Filed: Mar. 23, 2015; and U.S. Application Ser. No.: 14/664,991; Filed: Mar. 23, 2015; the contents of each of which are herein incorporated by reference in their entirety.

BACKGROUND

The present disclosure relates to the adjustment of helmet parameters to mitigate the risk of brain injuries, and more specifically, to methods, systems and computer program products for the automatic adjustment of helmet parameters based on a category of play to mitigate the risk of brain injuries.

Generally speaking, safety is a primary concern for both users of helmets and manufacturers of helmets. Helmets are used by individuals that participate in activities that have risk of head trauma, such as the area of sports, biking, motorcycling, etc. While helmets have traditionally been used to provide protection from blunt force trauma to the head, an increased awareness of concussion causing forces has motivated a need for advances in helmet technology to provide increased protection against concussions. A concussion is a type of traumatic brain injury that is caused by a blow to the head that shakes the brain inside the skull due to linear or rotational accelerations. Recently, research has linked concussions to a range of health problems, from depression to Alzheimer's, along with a range of brain injuries. Unlike severe traumatic brain injuries, which result in lesions or bleeding inside the brain and are detectable using standard medical imaging, a concussion is often invisible in brain tissue, and therefore only detectable by means of a cognitive change, where that change is measurable by changes to brain tissue actions, either neurophysiological or through muscle actions caused by the brain and the muscles resulting effects on the environment, for example, speech sounds.

Currently available helmets include a hard outer shell and internal padding that is designed to mitigate the risk of brain injuries. These helmets are designed to accommodate all types of impacts regardless of the probability of the occurrence of specific impacts during various types of usage.

SUMMARY

In accordance with an embodiment, a method for the automatic adjustment of helmet parameters based on a category of play includes monitoring a plurality of sensors in a helmet and determining the category of play for a user of the helmet based on data received from the plurality of sensors. Aspects further include automatically adjusting one or more parameters of the helmet based on the category of play.

In accordance with another embodiment, an adjustable helmet for mitigating the risk of brain injuries includes a processor and one or more sensors, the processor configured for performing a method. The method includes monitoring a plurality of sensors in a helmet and determining the category of play for a user of the helmet based on data received from the one or more of sensors. Aspects further include automatically adjusting one or more parameters of the helmet based on the category of play.

In accordance with a further embodiment, a computer program product for the automatic adjustment of helmet parameters based on a category of play includes a non-transitory storage medium readable by a processing circuit and storing instructions for execution by the processing circuit for performing a method. The method includes monitoring a plurality of sensors in a helmet and determining the category of play for a user of the helmet based on data received from the plurality of sensors. Aspects further include automatically adjusting one or more parameters of the helmet based on the category of play.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

In accordance with exemplary embodiments of the disclosure, methods, systems and computer program products for the automatic adjustment of helmet parameters based on a category of play are provided. In exemplary embodiments, the helmets include one or more sensors and one or more adjustable parameters, such as an adjustable chin strap or adjustable internal or external padding. In exemplary embodiments, the sensors may include one or more accelerometers, gyroscopes, or the like. In one embodiment, the outputs of the sensors are provided to a processor that monitors one or more physical movements or actions of the user and determines a category of play of the user of the helmet. In other embodiments, the category of play of the user may be provided to the helmet by the user or by another source. In exemplary embodiments, the processor makes adjustments to a protection profile of the helmet based on the category of play. The protection profile of the helmet may include, but is not limited to, the tightness of the chin strap, the size of one or more pads of the helmet, the stiffness of one or more pads of the helmet and the lateral mobility of one or more pads of the helmet. In exemplary embodiments, the protection profile for each category of play can be determined based on a probability of certain types of impacts and events occurring during each category of play.

Figure 1:
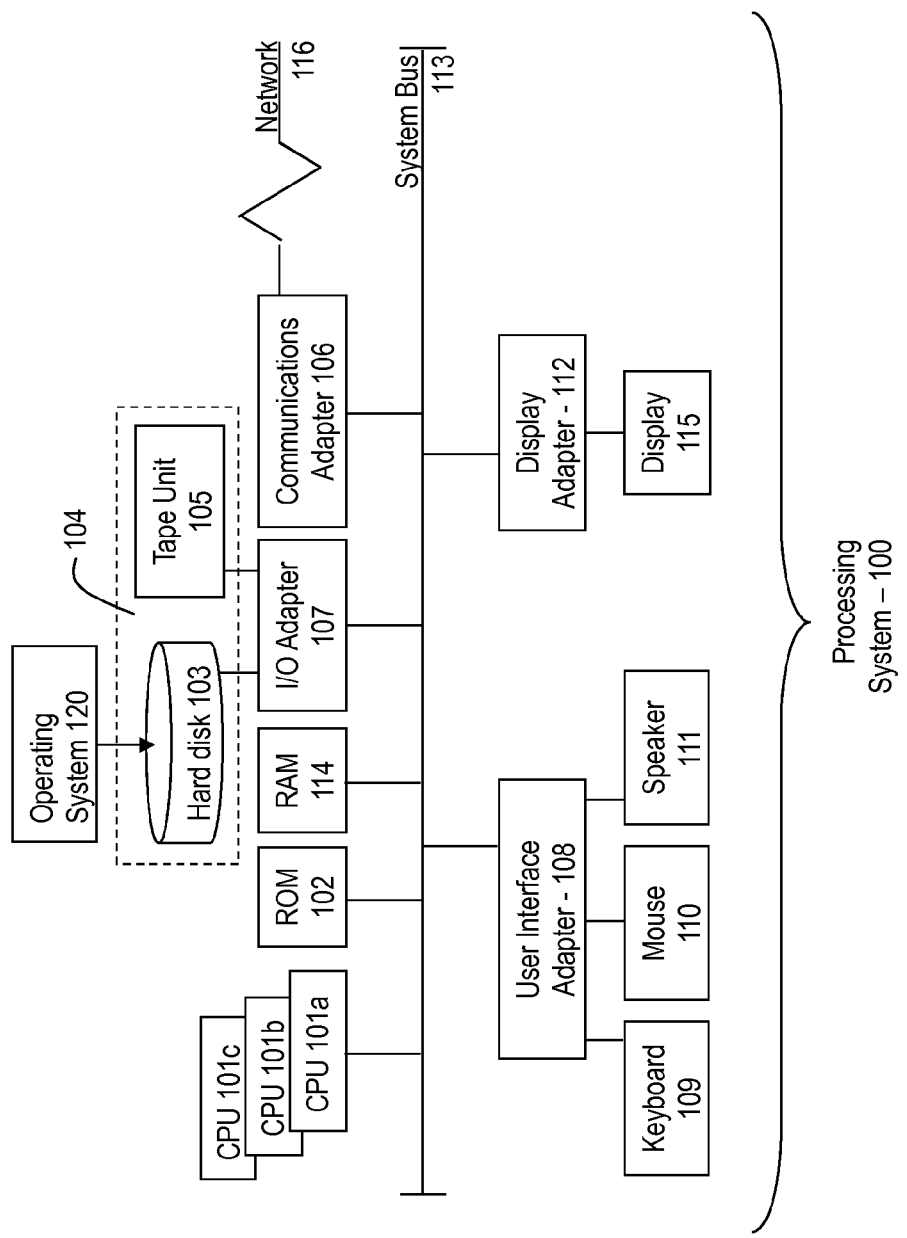
FIG. 1 is a block diagram illustrating one example of a processing system for practice of the teachings herein.

Referring to FIG. 1, there is shown an embodiment of a processing system 100 for implementing the teachings herein. In this embodiment, the system 100 has one or more central processing units (processors) 101a, 101b, 101c, etc. (collectively or generically referred to as processor(s) 101). In one embodiment, each processor 101 may include a reduced instruction set computer (RISC) microprocessor. Processors 101 are coupled to system memory 114 and various other components via a system bus 113. Read only memory (ROM) 102 is coupled to the system bus 113 and may include a basic input/output system (BIOS), which controls certain basic functions of system 100.

FIG. 1 further depicts an input/output (I/O) adapter 107 and a network adapter 106 coupled to the system bus 113. I/O adapter 107 may be a small computer system interface (SCSI) adapter that communicates with a hard disk 103 and/or tape storage drive 105 or any other similar component. I/O adapter 107, hard disk 103, and tape storage device 105 are collectively referred to herein as mass storage 104. Operating system 120 for execution on the processing system 100 may be stored in mass storage 104. A network adapter 106 interconnects bus 113 with an outside network 116 enabling data processing system 100 to communicate with other such systems. A screen (e.g., a display monitor) 115 is connected to system bus 113 by display adaptor 112, which may include a graphics adapter to improve the performance of graphics intensive applications and a video controller. In one embodiment, adapters 107, 106, and 112 may be connected to one or more I/O busses that are connected to system bus 113 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 113 via user interface adapter 108 and display adapter 112. A keyboard 109, mouse 110, and speaker 111 all interconnected to bus 113 via user interface adapter 108, which may include, for example, a Super I/O chip integrating multiple device adapters into a single integrated circuit.

Thus, as configured in FIG. 1, the system 100 includes processing capability in the form of processors 101, storage capability including system memory 114 and mass storage 104, input means such as keyboard 109 and mouse 110, and output capability including speaker 111 and display 115. In one embodiment, a portion of system memory 114 and mass storage 104 collectively store an operating system such as the AIX® operating system from IBM Corporation to coordinate the functions of the various components shown in FIG. 1.

Figure 2:
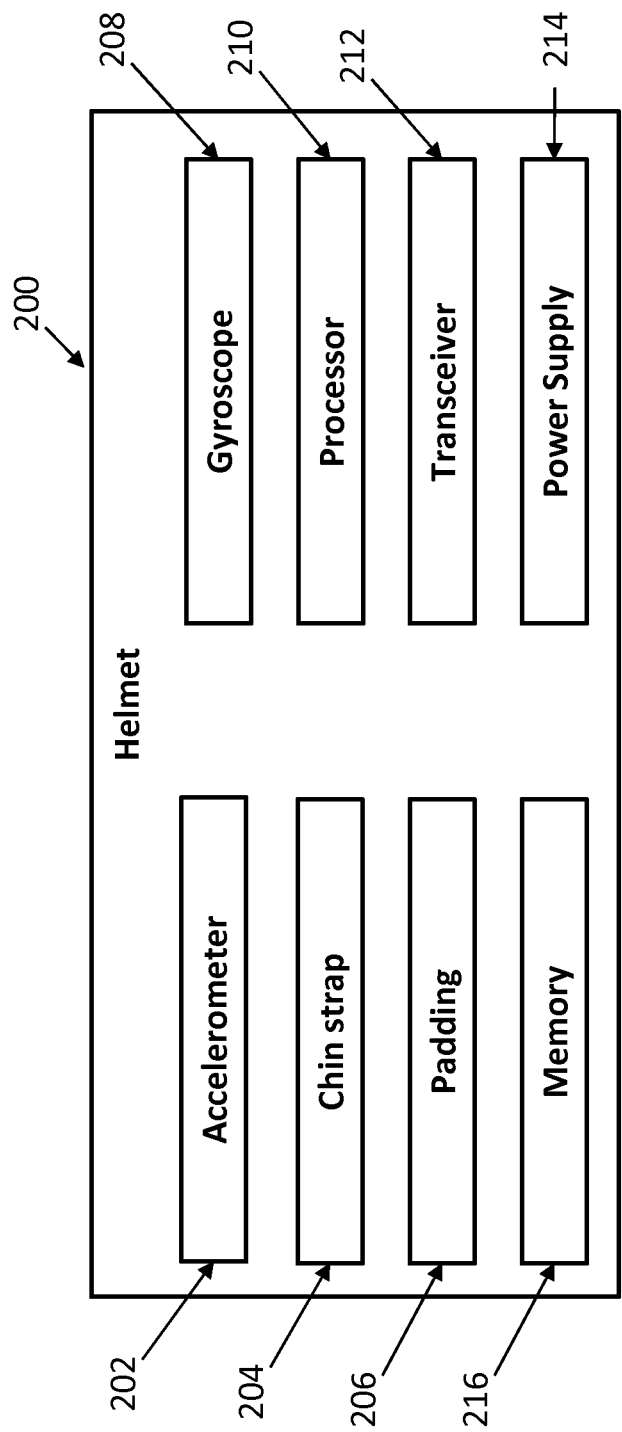
FIG. 2 is a block diagram illustrating an adjustable helmet in accordance with an exemplary embodiment.

Referring to FIG. 2, a block diagram illustrating an adjustable helmet 200 in accordance with an exemplary embodiment is shown. The term "helmet" may include, but is not intended to be limited to, a football helmet, a motorcycle helmet or the like. In exemplary embodiments, the adjustable helmet 200 includes one or more of the following: an accelerometer 202, a chin strap 204, a padding 206, a gyroscope 208, a processor 210, a transceiver 212, a power supply 214 and a memory 216. In exemplary embodiments, the power supply 214 may be a battery configured to provide power to one or more of the accelerometer 202, the gyroscope 208, the processor 210 and the transceiver 212.

In one embodiment, the processor 210 is configured to receive an output from one or more of the accelerometer 202 and the gyroscope 208 and to determine a category of play of the user of the adjustable helmet 200. In other embodiments, the processor 210 may be provided with the category of play of the user of the adjustable helmet 200 or the helmet may receive the category of play from an external processing system via the transceiver 212. As used herein, the term category of play means the manner in which the user is using the helmet. In one example, for a football helmet, the category of play may refer to the position being played by the user, running back, wide receiver, linemen, etc., or by the current activity being performed by the user, running, blocking, jumping, etc.

In exemplary embodiments, the padding 206 of the adjustable helmet 200 may include either or both of internal padding or external padding that can have one or more adjustable parameters. In one embodiment, the padding 206 may include electroactive polymers that can be used to change the size, shape, and/or stiffness of the padding 206. In another embodiment, the padding 206 may include inflatable padding that can be inflated and deflated by the adjustable helmet 200. In additional embodiments, the padding 206 may be coupled to the helmet 200 by a liner that can be adjusted to selectively allow the padding 206 to move laterally in relation to the shell of the helmet. For example, the liner may be configured to allow the padding to slide, or slip, along the surface of the shell of the helmet to reduce the torque on the user's head during an impact. In exemplary embodiments, the degree, or amount of lateral movement, of the liner with respect to the shell may be automatically adjusted based on the category of play of the user of the helmet.

Figure 3:
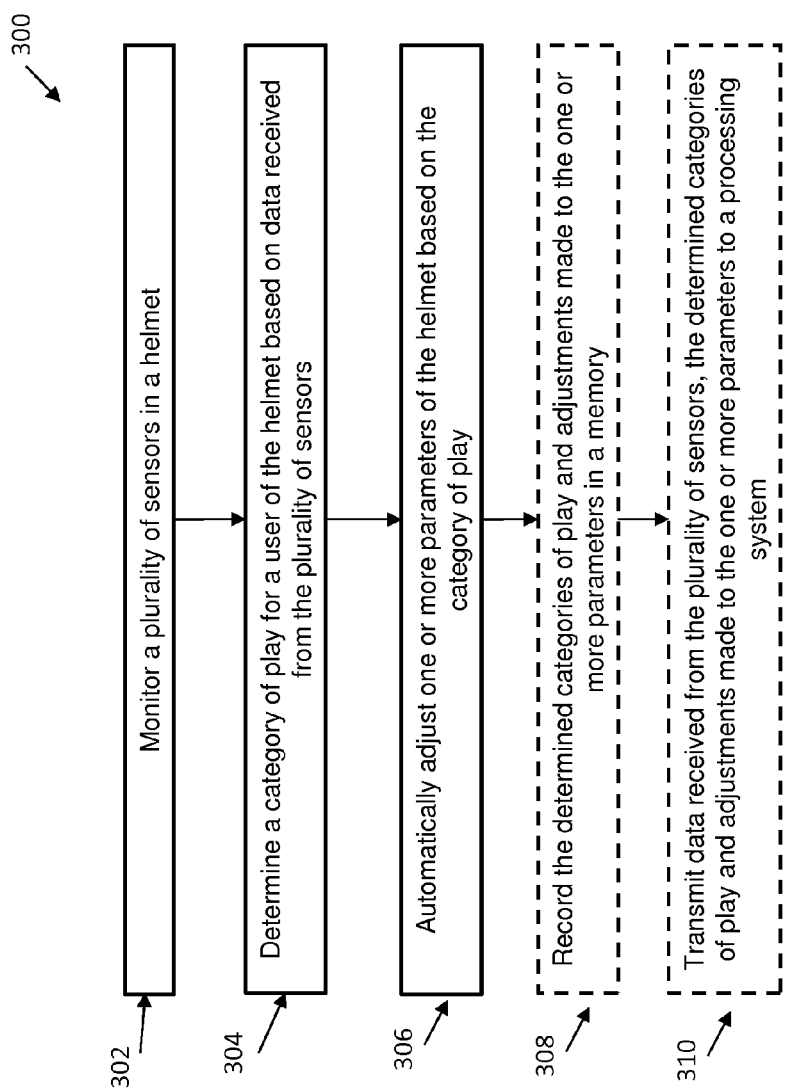
FIG. 3 is a flow diagram of a method for the automatic adjustment of helmet parameters based on a category of play in accordance with an exemplary embodiment.

Referring now to FIG. 3, a flow diagram of a method 300 for the automatic adjustment of helmet parameters based on a category of play in accordance with an exemplary embodiment is shown. As shown at block 302, the method 300 includes monitoring a plurality of sensors in an adjustable helmet. In exemplary embodiments, the plurality of sensors includes one or more of an accelerometer and a gyroscope. Next, as shown at block 304, the method 300 includes determining a category of play for a user of the helmet based on data received from the plurality of sensors. In exemplary embodiments, the processor of the adjustable helmet may create a baseline profile of the user during each category of play based on input form the accelerometer and the gyroscope and may store the baseline profile in the memory. The processor may compare the readings from the accelerometer and the gyroscope with the stored baseline profile to determine the category of play for a user.

Continuing with reference to FIG. 3, as shown at block 306, the method 300 includes automatically adjusting one or more parameters of the helmet based on the category of play. In exemplary embodiments, the adjustments may include, but are not limited to, adjusting the stiffness on the padding, adjusting the tightness of the chin strap, adjusting the size of the padding, etc. The type and amount of an adjustment is chosen based on a model of expected risks given certain plays to certain types of hits and accelerations to mitigate the brain injury from these hits and accelerations. The adjustments to the padding may be uniform or non-uniform, i.e., the stiffness of all of the padding may not be the same. For example, based on the category of play the stiffness of the padding in the front portion of the helmet may be greater or less that the stiffness in the back of the helmet.

Optionally, the method 300 may include storing the determined states of play and adjustments made to the one or more parameters in a memory, as shown in block 308. In addition, the method 300 may also include transmitting the data received from the plurality of sensors, the determined categories of play and adjustments made to the one or more parameters to a processing system, as shown at block 310.

Figure 4:
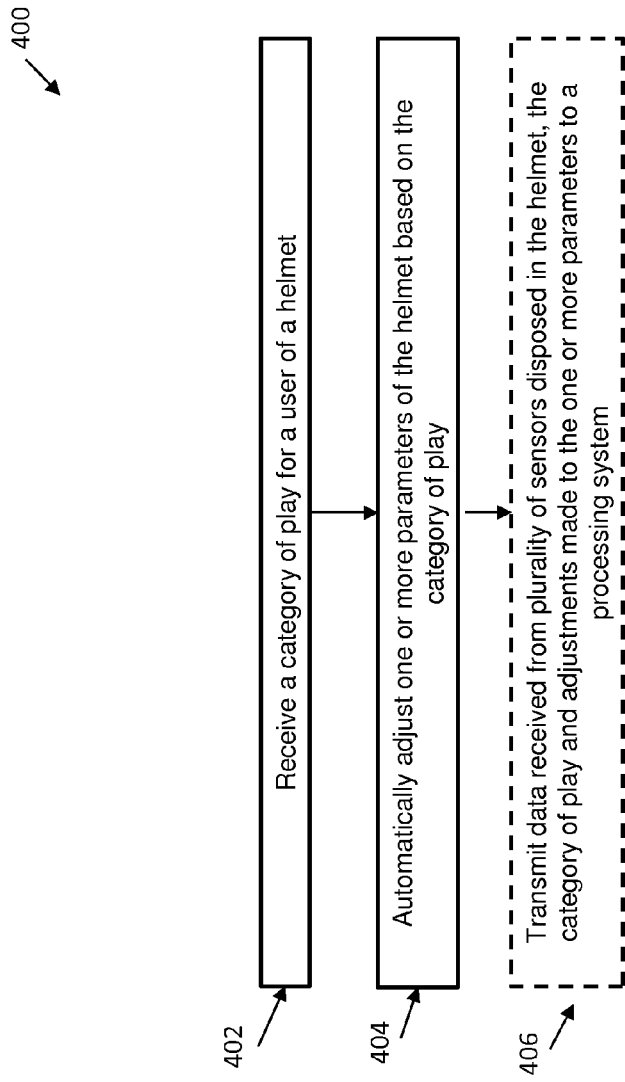
FIG. 4 is a flow diagram of another method for automatic adjustment of helmet parameters based on a category of play in accordance with an exemplary embodiment.

Referring now to FIG. 4, a flow diagram of another method 400 for the automatic adjustment of helmet parameters based on a category of play in accordance with an exemplary embodiment is shown. As shown at block 402, the method 400 includes receiving a category of play for a user of a helmet. For example, the helmet may receive an input from the user that indicates the category of play or the helmet may receive input from a separate processing system via a transmitter that indicates the category of play. Next, as shown at decision block 404, the method 400 includes automatically adjusting one or more parameters of the helmet based on the category of play. In exemplary embodiments, the adjustments may include, but are not limited to, adjusting the stiffness on the padding, adjusting the tightness of the chin strap, adjusting the size of the padding, etc. The type and amount of an adjustment is chosen based on a model of expected risks given certain plays to certain types of hits and accelerations to mitigate the brain injury from these hits and accelerations. The adjustments to the padding may be uniform or non-uniform, i.e., the stiffness of all of the padding may not be the same. For example, based on the category of play the stiffness of the padding in the front portion of the helmet may be greater or less that the stiffness in the back of the helmet. Optionally, the method 400 may include transmitting data received from plurality of sensors disposed in the helmet, the category of play and adjustments made to the one or more parameters to a processing system, as shown in block 406.

In exemplary embodiments, the processor of the helmet may use a risk/probability function that is constructed based on the category of play a wearer is engaged in to determine the parameters for the adjustable helmet for certain hits and certain angles of acceleration. In one embodiment, such as that shown in FIG. 4, the risk/probability function may receive a direct input of category of play, e.g. from a quarterback calling a certain play, or from a motorcycle signaling its speed, turn frequency, aggressiveness of the rider, ice on road, etc. In one embodiment, such as that shown in FIG. 3, the risk/probability function may include making a determination of the category of play based on data received from one or more sensors disposed in the helmet.

Figure 5:
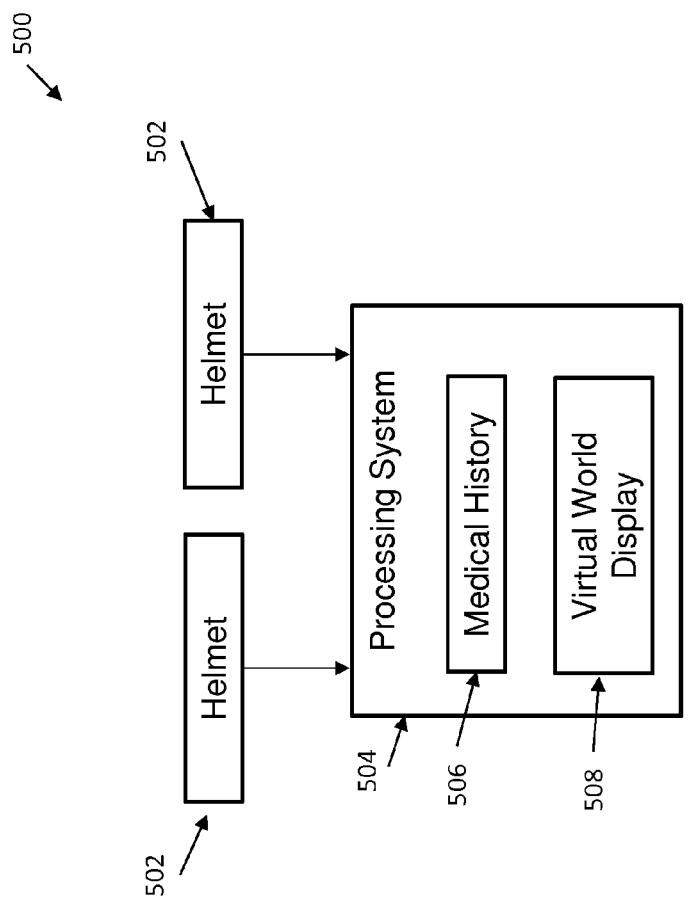
FIG. 5 is a block diagram illustrating a system for monitoring adjustable helmets in accordance with an exemplary embodiment.

Referring now to FIG. 5, a block diagram illustrating a system 500 for monitoring adjustable helmets in accordance with an exemplary embodiment is shown. As illustrated the system 500 includes one or more adjustable helmets 502, such as the one shown and described above with reference to FIG. 2, and a processing system 504, such as the one shown and described above with reference to FIG. 1. The processing system 504 is configured to communicate with the helmets 502 and is also configured to store the medical history 506 of the users of the helmets 502. In exemplary embodiments, the medical history 506 of the users of the helmets 502 may be used by the helmet in determining what adjustments to make to the helmet during play. In addition, the processing system 504 may include a virtual world display 508 that is configured to provide a display a real-time status of each of the users of the helmets. In exemplary embodiments, the status may include the category of play of each user, any indications that the user may have suffered a traumatic brain injury, a duration of play of the user, a duration that the user has been in the current category of play, or the like.

In exemplary embodiments, the user's history of collision or medical concerns may be used to determine a traumatic brain injury risk assessment, either by the embedded processor or the separate processing system. In addition, the helmet may be configured to provide a real-time feed of the user's cognitive state to increase the confidence level of the need for a particular alert or indication. In exemplary embodiments, an aggregate indication may be used to summarize an overall state of a group of players. This may also help to potentially identify area of risk in the dynamics of player-player interaction, overly aggressive players, playing field conditions, etc. In exemplary embodiments, an automatic feed from a user's history of collision or medical concerns may also be provided to a processor of the helmet in order to update an impact risk model for each category of play. In addition, the processing system 504 may receive a real-time feed of the user's cognitive state, which can be used to update the risk models used by the helmets. The risk models may also be sent to the virtual world display 508 of the game and players, which allows the sports staff health professionals to visualize the nature of potential problems.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer program product for automatic adjustment of helmet parameters based on a category of play, the computer program product comprising:
 a non-transitory storage medium readable by a processing circuit and storing instructions for execution by the processing circuit for performing a method comprising:
 monitoring a plurality of sensors in a helmet;
 determining the category of play for a user of the helmet based on data received from the plurality of sensors; and
 automatically adjusting parameters of the helmet based on the category of play, wherein the parameters include at least one of a stiffness, a size and a shape of a padding of the helmet,
 wherein a type of an adjustment and an amount of the adjustment are determined based on a model of expected risks for the category of play for the user.

2. The computer program product of claim 1, wherein the padding is disposed on an internal surface of the helmet.

3. The computer program product of claim 1, the stiffness of the padding on the helmet includes increasing the stiffness in a first area of the padding and decreasing the stiffness in a second area of the padding.

4. The computer program product of claim 1, wherein automatically adjusting one or more parameters of the helmet based on the category of play includes adjusting a tightness of a chin strap of the helmet.

5. The computer program product of claim 4, wherein the one or more parameters are adjusted based on a risk profile associated with the category of play.

6. The computer program product of claim 5, wherein the risk profile is further based on a medical history of the user of the helmet.

7. An adjustable helmet for mitigating the risk of brain injuries, comprising:
 a processor and one or more sensors, the processor configured to:
 monitoring the one or more sensors;
 determine a category of play for a user of the helmet based on data received from the plurality of sensors; and
 automatically adjust parameters of the helmet based on the category of play, wherein the parameters include at least one of a stiffness, a size and a shape of a padding of the helmet,
 wherein a type of an adjustment and an amount of the adjustment are determined based on a model of expected risks for the category of play for the user.

8. The helmet of claim 7, wherein the padding is disposed on an internal surface of the helmet.

9. The helmet of claim 7, the stiffness of the padding on the helmet includes increasing the stiffness in a first area of the padding and decreasing the stiffness in a second area of the padding.

10. The helmet of claim 7, wherein the one or more parameters are adjusted based on a risk profile associated with the category of play.

11. The helmet of claim 10, wherein the risk profile is further based on a medical history of the user of the helmet.

\* \* \* \* \*